United States Patent
Ross

(10) Patent No.: US 9,433,544 B1
(45) Date of Patent: Sep. 6, 2016

(54) GARMENT WITH TEAR-OFF BANDAGE

(71) Applicant: Sheila Ross, Monrovia, CA (US)

(72) Inventor: Sheila Ross, Monrovia, CA (US)

( * ) Notice: Subject to any disclaimer, the term of this patent is extended or adjusted under 35 U.S.C. 154(b) by 233 days.

(21) Appl. No.: 14/194,190

(22) Filed: Feb. 28, 2014

(51) Int. Cl.
    *A61F 15/00* (2006.01)

(52) U.S. Cl.
    CPC ........... *A61F 15/002* (2013.01); *A61F 15/006* (2013.01)

(58) Field of Classification Search
    CPC ........ A61F 13/085; A61F 13/00; A61F 5/34; A61F 13/08; A61F 13/145; A61F 13/069; A61F 2007/0002; A61F 2007/0018; A61F 2007/006; A61F 2007/0063; A61F 2007/0069; A61F 2007/0076; A61F 2007/00; A61B 5/1116; A61B 5/112; A61B 5/1126; A61B 5/4528; A61B 17/1322; A61B 17/1325; A61B 5/01; A61B 5/1118; A61B 5/441; A61B 5/4866; A61B 5/6843; A61B 6/505; A61B 8/0875; A61B 8/4472
    USPC .................................... 602/42; 606/201, 204
    See application file for complete search history.

(56) References Cited

U.S. PATENT DOCUMENTS

| 2,339,239 | A | 1/1944 | Carmichael |
| 3,793,644 | A | 2/1974 | Kellner |
| 6,009,560 | A | 1/2000 | McKenney |
| 7,981,135 | B2 * | 7/2011 | Thorpe ............... A61B 17/1322 606/203 |
| 8,465,514 | B1 | 6/2013 | Rose |
| 2007/0028343 | A1 | 2/2007 | Makowka |
| 2008/0221612 | A1 * | 9/2008 | Rose ................... A61B 17/1322 606/203 |
| 2008/0243172 | A1 | 10/2008 | Thorpe |
| 2011/0270299 | A1 * | 11/2011 | Rose ........................ A41D 1/08 606/203 |
| 2012/0309850 | A1 | 12/2012 | Rinke |

FOREIGN PATENT DOCUMENTS

CN            201286736 Y  *  8/2009

* cited by examiner

*Primary Examiner* — Michael Brown
(74) *Attorney, Agent, or Firm* — QuickPatents, LLC; Kevin Prince

(57) ABSTRACT

A garment for bandaging a wound on a member of a mammal includes a flexible garment portion, and may take the form of a shirt, shorts, pants, a vest, or the like. At least one perforation in the garment portion defines at least one tear-away bandage comprising an outer surface, an inner surface, two opposing ends and a central section. The inner surface of the central section is adapted for application to the wound, and the two opposing ends are adapted for tying around the member of the mammal. Preferably the at least one bandage comprises a plurality of layers, including a netting material adapted for contacting the wound at the central section. In one embodiment, an absorbent layer of the at least one bandage is sandwiched between the inner surface or an inner layer and the outer surface or an outer layer.

17 Claims, 3 Drawing Sheets

GARMENT WITH TEAR-OFF BANDAGE

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to garments, and more particularly to a garment with break-away bandages.

DISCUSSION OF RELATED ART

Outdoor recreational and sporting events sometimes result in injury to the participants. For example, mountain bike riding can be dangerous over uneven and unexpected terrain, location access to a proper bandage is unavailable, and if the injury is significant a garment such as a sock or T-shirt may be sacrificed and used as a makeshift bandage.

A garment having defined, tear-away bandages would be useful in such situations, but no such prior art exists. US Patent Application 2007/0028343 to Makowka on Feb. 8, 2007 teaches a disposable protective garment having tear-away sections intended for adjusting the size of the garment. Such tear-away sections are non-linear and not well-suited for use as a bandage. Moreover, such a garment is a disposable garment, not suitable for wearing while participating in a sporting event, hiking, or other physical activities.

US Patent Application 2008/0243172 to Thorpe on Oct. 2, 2008 teaches a garment having an affixed tourniquet. Only a small minority of injuries is so severe that a tourniquet is required. Indeed, such a garment is intended for use on a battlefield where such injuries are much more commonplace than in non-war settings. Such a device would be wholly unsuited for use to stop the bleeding of a cut, for example, and does not provide for a bandaging function.

Therefore, there is a need for a garment that includes one or more tear-away bandages that can be used to temporarily bandage a wound when more conventional bandages are not available. Such a needed garment would include bandages with absorbent material and mesh "breathable" material to help absorb blood but not exacerbate the injury. The bandages of such a needed invention would be visually subtle, allowing the garment to be principally used as a garment and only separated into bandages when absolutely necessary, perhaps never. Such a needed invention would be comfortable to wear and would be machine washable, just as any other garment. The present invention accomplishes these objectives.

SUMMARY OF THE INVENTION

The present device is a garment for bandaging a wound on a member of a mammal, such as an arm or leg of a person or pet. The garment includes a flexible garment portion, and may take the form of a shirt, shorts, pants, a vest, or the like.

At least one perforation in the garment portion defines at least one tear-away bandage. The at least one bandage comprises an outer surface, an inner surface, two opposing ends and a central section. The inner surface of the central section is adapted for application to the wound, and the two opposing ends are adapted for tying around the member of the mammal. Preferably the two opposing ends of the at least one bandage are thinner than the central section of the at least one bandage. In one embodiment, each end of the at least one bandage includes a plurality of cooperative mechanical fasteners, such that the size or tightness of the bandage about the member of the mammal may be adjusted.

Preferably the garment includes a plurality of the bandages, each such bandage alternating in orientation about the garment so that the thin opposing ends of one of the of the perforations may be substantially parallel to an edge of the garment, such as a torso or sleeve edge of the shirt for example.

Preferably the at least one bandage comprises a plurality of layers, including a netting material adapted for contacting the wound at the central section. At least another of the plurality of layers comprises a flexible, absorbent material such as a flexible cotton web material, a flexible fleece web material, a flexible mesh web material, a polyester material, a nylon material, a spandex-type material, a rayon-type material, an acrylic material, a cotton material, a synthetic material, or the like. In one embodiment, an absorbent layer of the at least one bandage is sandwiched between the inner surface or an inner layer and the outer surface or an outer layer.

The present invention is a garment that includes one or more tear-away bandages that can be used to temporarily bandage a wound when more conventional bandages are not available. The present invention includes bandages with absorbent material and mesh "breathable" material to help absorb blood but not exacerbate the injury. The bandages of the present invention are visually subtle, allowing the garment to be principally used as a garment and only separated into bandages when absolutely necessary. As such, the present garment is comfortable to wear and is machine washable. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
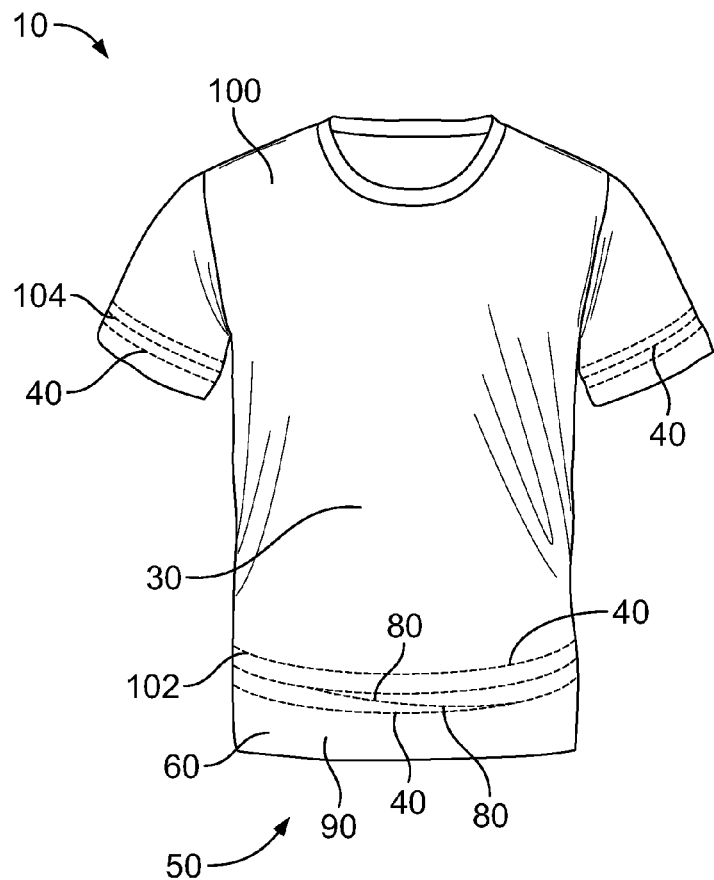
FIG. 1 is a perspective view of one embodiment of the invention.
Figure 2:
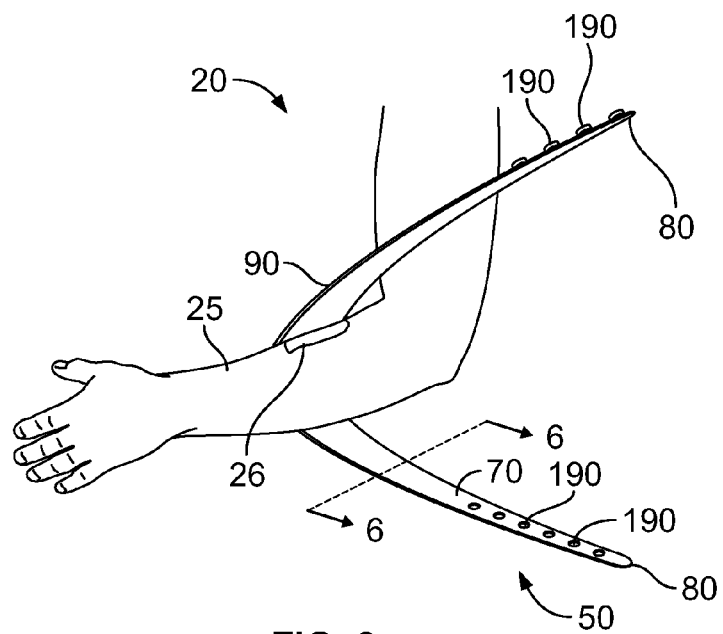
FIG. 2 is a perspective view of a bandage separated from a garment of the invention and as being applied to a wound on a person.

FIGS. 1 and 2 illustrate a garment 10 for bandaging a wound 26 on a member 25 of a mammal 20, such as an arm or leg of a person or pet. The garment 10 includes a flexible garment portion 30, and may take the form of a shirt 100, shorts 110 (FIG. 3), pants 120 (FIG. 4), a vest 130 (FIG. 5), or the like.

Figure 6:
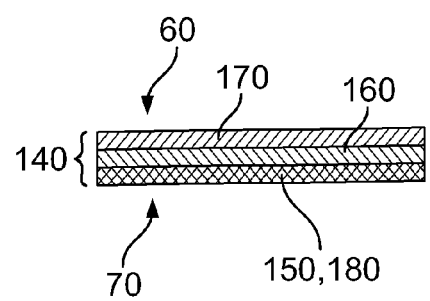
FIG. 6 is a cross-sectional view of the invention, taken generally along lines 6-6 of FIG. 2.

At least one perforation 40 in the garment portion 30 defines at least one tear-away bandage 50. The at least one bandage 50 comprises an outer surface 60 (FIG. 6), an inner surface 70, two opposing ends 80 and a central section 90. The inner surface 70 of the central section 90 is adapted for application to the wound 26, and the two opposing ends 80 are adapted for tying around the member 25 of the mammal 20. Preferably the two opposing ends 80 of the at least one bandage 50 are thinner than the central section 90 of the at least one bandage 50, which allows the ends 80 of the bandage 50 to be more easily tied around the member 26. In one embodiment, each end 80 of the at least one bandage 50 includes a plurality of cooperative mechanical fasteners 190 (FIG. 2), such as mechanical snaps, hook-and-loop type fastening material, or the like. As such, the size or tightness of the bandage 50 about the member 26 of the mammal 20 may be adjusted as necessary.

Preferably the garment 10 includes a plurality of the bandages 50, each such bandage 50 alternating in orientation about the garment 10 so that the thin opposing ends 80 of one of the bandages 50 is adjacent to the thicker central section 90 of an adjacent bandage 50. As such, most of the perforations 40 may be substantially parallel to an edge of the garment 10, such as a torso or sleeve edge of the shirt 100 for example.

Figure 3:
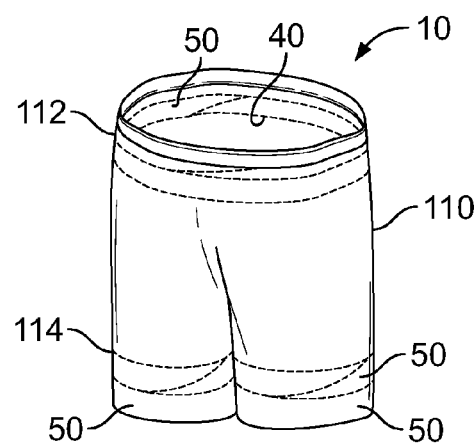
FIG. 3 is a perspective view of an alternate embodiment of the invention.
Figure 4:
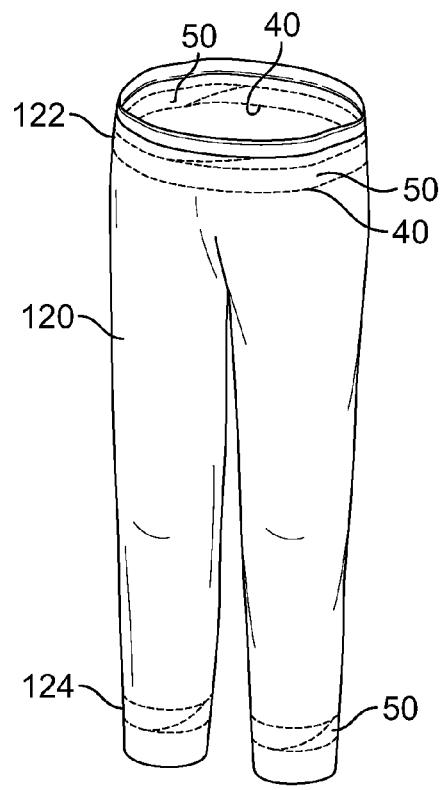
FIG. 4 is a perspective view of another alternate embodiment of the invention.
Figure 5:
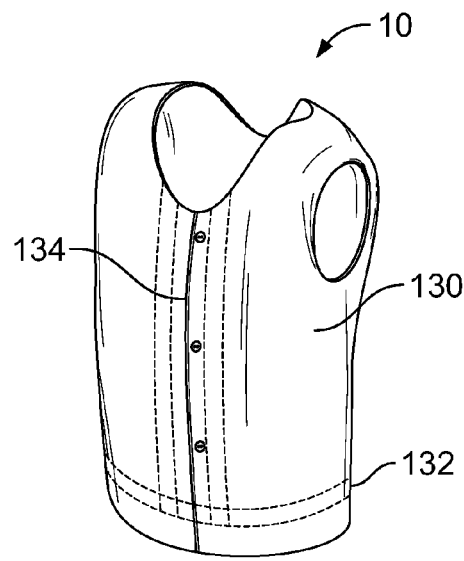
FIG. 5 is perspective view of yet another alternate embodiment of the invention.

The at least one bandage 50 may be positioned around a torso area 102 of the garment 10 taking the form of the shirt 100 (FIG. 1). Alternately, or additionally, the at least one bandage 50 may be positioned around a sleeve area 104 of the shirt 100. The at least one bandage 50 may be positioned around a leg area 114 of the garment 10 taking the form of the shorts 110 (FIG. 3). Alternately, or additionally, the at least one bandage 50 may be positioned around a torso areas 112 of the shorts 110. The at least one bandage 50 may be positioned around a leg area 124 of the garment 10 taking the form of the pants 120 (FIG. 4). Alternately, or additionally, the at least one bandage 50 may be positioned around a torso areas 122 of the pants 120. The at least one bandage 50 may be positioned around a torso area 132 of the garment 10 taking the form of the vest 130 (FIG. 5). Alternately, or additionally, the at least one bandage 50 may be positioned around a chest area 134 of the vest 130.

Preferably the at least one bandage 50 comprises a plurality of layers 140 (FIG. 6), including a netting material 150 adapted for contacting the wound 26 at the central section 90. At least another of the plurality of layers 140 comprises a flexible, absorbent material 160 such as a flexible cotton web material, a flexible fleece web material 170, a flexible mesh web material 180, a polyester material, a nylon material, a spandex-type material, a rayon-type material, a cotton material, an acrylic material, a synthetic material, or the like. In one embodiment, an absorbent layer 140 of the at least one bandage 50 is sandwiched between the inner surface 70 or an inner layer 140 and the outer surface 60 or an outer layer 140.

Figure 7:
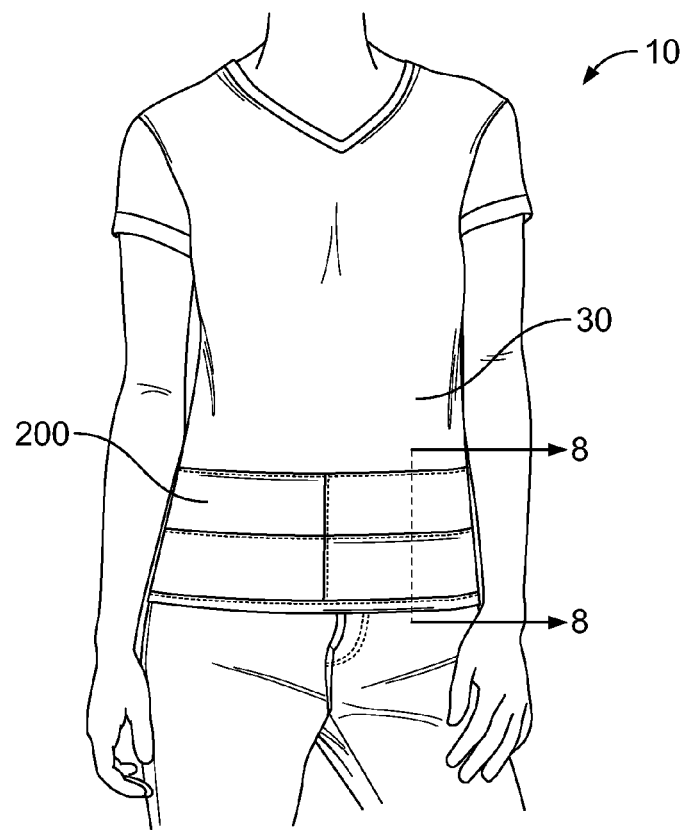
FIG. 7 is a front elevational view of a yet another alternate embodiment of the invention.
Figure 8:
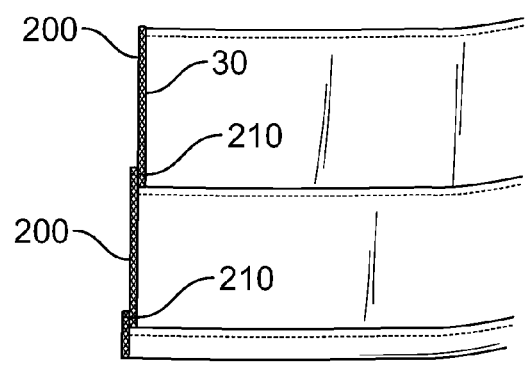
FIG. 8 is a cross-sectional view of the embodiment of FIG. 7, taken generally along lines 8-8.

In one embodiment, illustrated in FIGS. 7 and 8, the garment 10 comprises the flexible garment portion 30 and at least one break-away bandage 200 releasably affixed therewith. Preferably the at least one break-away bandage 200 is affixed to the garment portion 30 with a thread 210 stitched through and/or around the garment portion 30 and the at least one break-away bandage 200 and adapted to be pulled away from the garment 10 manually. As such, upon pulling the thread 210 away from the garment 10, the at least one break-away bandage 200 is released from the garment portion 30.

While a particular form of the invention has been illustrated and described, it will be apparent that various modifications can be made without departing from the spirit and scope of the invention. For example, certain styles of garments are shown in the drawings, but other types of garments, such as hats, scarves, gloves, or the like may be utilized without departing from the scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A garment for bandaging a wound on a member of a mammal, the garment comprising:
   a flexible garment portion; and
   at least one perforation in the garment portion defining at least one tear-away bandage, the at least one bandage comprising an outer surface and an inner surface, and further comprising two opposing ends and a central section, the inner surface of the central section adapted for application to a wound, and the two opposing ends adapted for tying around the member of the mammal;
   wherein the at least one bandage comprises a plurality of layers, at least one of the plurality of layers comprising a netting material adapted for contacting the wound at the central section, and at least another of the plurality of layers comprising a flexible, absorbent material.

2. The garment of claim 1 wherein the two opposing ends of the at least one bandage are thinner than the central section of the at least one bandage.

3. The garment of claim 2 wherein the at least one tear-away bandage is a plurality of bandages, each bandage alternating in orientation about the garment so that thin opposing ends of one of the bandages is adjacent to the thicker central section of an adjacent bandage.

4. The garment of claim 1 wherein the garment takes the form of a shirt, and wherein the at least one bandage is positioned around a torso area of the shirt.

5. The garment of claim 1 wherein the garment takes the form of a shirt, and wherein the at least one bandage is positioned around a sleeve area of the shirt.

6. The garment of claim 1 wherein the garment takes the form of a pair of shorts, and wherein the at least one bandage is positioned around a leg area of the shorts.

7. The garment of claim 1 wherein the garment takes the form of a pair of shorts, and wherein the at least one bandage is positioned around a torso area of the shorts.

8. The garment of claim 1 wherein the garment takes the form of a pair of pants, and wherein the at least one bandage is positioned around a leg area of the pants.

9. The garment of claim 1 wherein the garment takes the form of a pair of pants, and wherein the at least one bandage is positioned around a torso area of the pants.

10. The garment of claim 1 wherein the garment takes the form of a vest, and wherein the at least one bandage is positioned around a torso area of the vest.

11. The garment of claim 1 wherein the garment takes the form of a vest, and wherein the at least one bandage is positioned around a chest area of the vest.

12. The garment of claim 1 wherein at least one of the plurality of layers is made with at least one of a group of materials consisting of fleece, polyester, nylon, spandex, rayon, acrylic, mesh web material, or cotton.

13. The garment of claim 1 wherein an absorbent layer of the at least one bandage is fixed between an inner layer and an outer layer thereof.

14. The garment of claim 1 wherein the at least one tear-away bandage includes a plurality of cooperative mechanical fasteners on the opposing ends thereof, whereby the size of the bandage about the member of the mammal may be adjusted.

15. The garment of claim 1 wherein at least one of the plurality of layers is made with at least one of a group of materials consisting of polyester, nylon, spandex, rayon, acrylic, or cotton.

16. The garment of claim 1 wherein at least one of the plurality of layers is made with a synthetic material.

17. The garment of claim 1 wherein a thread is stitched through and/or around the perforations and adapted to be pulled away from the garment manually, whereby upon pulling the thread away from the garment and perforations, the perforations become readily visible and readily separable.

* * * * *